United States Patent [19]
Morrison et al.

[11] 3,937,971
[45] Feb. 10, 1976

[54] METHOD AND APPARATUS FOR MAKING A FOCUSED SHIELD

[76] Inventors: Richard A. Morrison, 9021 Delmar, Prairie Village, Kans. 66207; Cecil W. Johnston, 19710 Lake City Road, Independence, Mo. 64057

[22] Filed: Oct. 11, 1974

[21] Appl. No.: 514,109

[52] U.S. Cl. ............... 250/515; 29/557; 250/505; 250/520
[51] Int. Cl.² ................. G21C 11/00; H01J 35/16
[58] Field of Search ............... 250/515, 520, 505; 350/96 R; 29/557

[56] References Cited
UNITED STATES PATENTS
1,156,906  10/1915  Kelly .......................... 250/520

*Primary Examiner*—Harold A. Dixon

[57] ABSTRACT

A focused shield for use in connection with a radiation therapy machine or the like is constructed using a method and apparatus that results in a shield having a bevel-walled aperture. The aperture is cut into a focused shield blank and has a predetermined configuration corresponding to a selected area of a patient to be exposed to a field of radiation with the angularity of the aperture sidewalls relative to the radiation rays being such that any rays of a radiation beam in alignment with the aperture enter the same and do not strike the sidewalls thereof but rather pass through the aperture in an unimpeded manner. The method and apparatus employed in making the focused shield incorporates the use of a focused shield blank having a convexly rounded bottom side and a blank holding fixture, adapted for use with a band saw or the like, having a bowl-shaped concavity for receiving the blank and positioning the same on a surface that has a radius of curvatuve corresponding to the curvature of the blank bottom wall during the cutting of the aperture into the blank.

17 Claims, 6 Drawing Figures

METHOD AND APPARATUS FOR MAKING A FOCUSED SHIELD

This invention relates to a shield of the kind employed in connection with radiation therapy machines to limit the area of exposure of a patient to cobalt rays or the like such that the radiation rays only strike at the very exact spot intended on the human body. In order that the rays strike only the intended spots, lead shields are positioned between the source of the cobalt rays and the patient's body such that the shields serve to protect those areas of the body that are not to be treated.

Conventionally, focused shields are custom-made for each individual and contain an aperture therein having a configuration corresponding to the area of the body that is to be treated so that any cobalt rays directed to an area laterally of the aperture are blocked by the lead shield. Inasmuch as the patients normally require more than one treatment the shields must be very exact in order that the very same spot is uniformly and consistently exposed to the rays each time the patient is treated.

The lead shields, which are approximately 2 inches thick, are disposed to intersect a radiation beam and thus block off all rays except those which are in a position to pass through the aperture in the shield. However, because of the thickness of the shields, as conventionally known, all of the rays entering the aperture do not necessarily exit the same because their angular disposition relative to the shield and the aperture sidewalls is such that they strike a sidewall before they have a chance to exit the aperture. Also, because of this aforementioned angularity of the rays relative to the focused shield, which is normally disposed perpendicular to the central, longitudinal axis of the radiation beam, there is also a "dead" spot below that portion of the aperture where the upper or entry edge of the aperture intersects the radiation rays proximal thereto.

It is, therefore, a very important object of this invention to provide a method of fabricating a focused shield for use in connection with a radiation therapy machine or the like which the focused shield has a field of radiation aperture configured to permit precise exposure of a predetermined area of a patient's body and in which all of the radiation rays in alignment with the aperture pass therethrough to expose an area of the patient corresponding to the full area and configuration of the aperture.

Another very important object of the invention is to provide a focused shield having an aperture therein through which any rays entering the aperture also exit the aperture in an unimpeded manner.

It is another very important object of our invention to provide a method and apparatus for use in connection therewith for making a focused shield having an aperture therein that permits all radiation rays entering the aperture to exit therefrom in an unimpeded manner.

Yet another important object of the instant invention is to provide a focused shield, as well as a method and apparatus for making the same, in which the focused shield has an aperture in which the sidewalls thereof are disposed to permit all radiation rays in alignment with the aperture to pass therethrough.

A still further object of the instant invention is to provide a focused shield having a bevel-walled field of radiation aperture in which the sidewalls thereof are in substantial parallelism with the radiation rays passing through the aperture and proximal a sidewall thereof.

A still further object of our invention is to provide a focused shield blank holding fixture adapted especially for use with a band saw or the like to permit cutting an aperture having the desired radiation field outline in which the sidewalls of the aperture are automatically beveled in order that the sidewalls will be substantially parallel with the radiation rays passing thereby and proximal thereto when the focused shield is inserted in a radiation therapy machine.

Figure 5:
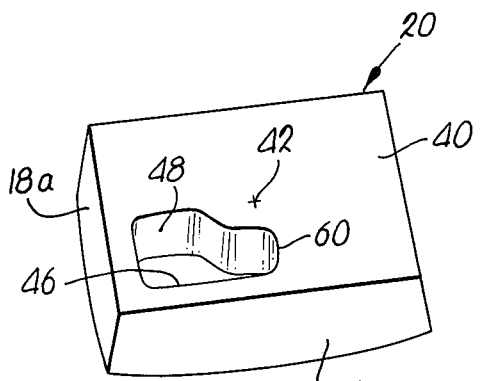
Figure 6:
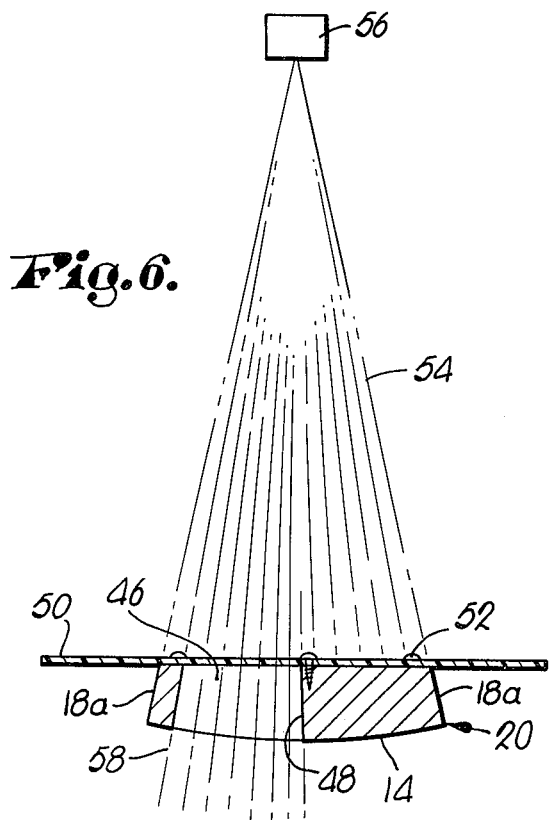

FIG. 5 is a top and edge perspective view showing a completed focused shield having a radiation field aperture and trimmed edges; and FIG. 6 is an elevational view with the focused shield and a holder therefor shown in section, illustrating the positioning of a focused shield and its holder relative to a radiation beam emanating from a source of radiation forming a part of a radiation therapy machine.

A focused shield blank 10 is preferably cast or molded from molten lead to present a generally rectangular body having a planar top side 12, a rounded bottom side 14 opposite the top side 12 and longitudinal and transverse edges 16 and 18, respectively, generally perpendicular to the planar top side 10. The shield blanks 10 may be uniformly cast having overall standard dimensions that are compatible with a radiation therapy machine (not shown) in connection with which the blanks 10 are to be ultimately used. If desired, the edges 16 and 18 may be subsequently trimmed for purposes of reducing weight if the full area of the blank 10 is not required. Normally the blanks 10 are at least 2 inches thick.

Figure 4:
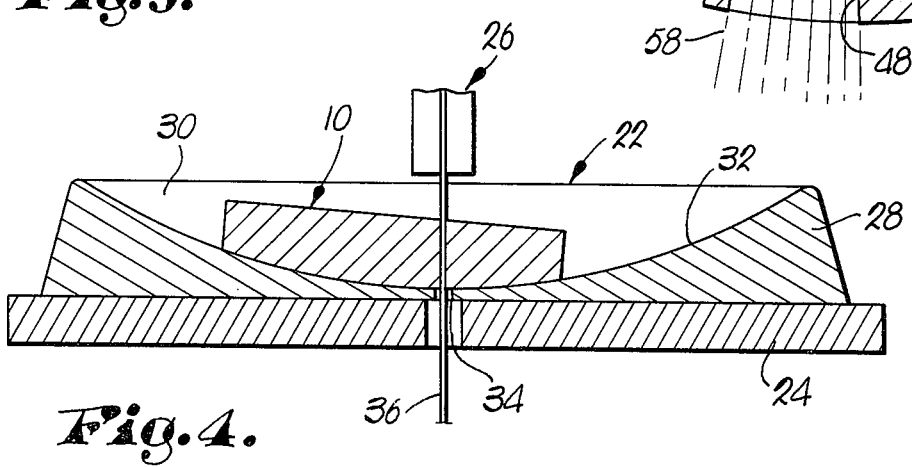
FIG. 4 is a fragmentary, vertical, cross-sectional view showing the focused shield blank holding fixture on the cutting table of a band saw with a focused shield blank positioned in a concavity of the fixture for cutting a radiation field aperture in the shield blank to make a focused shield.

The method of making a focused shield 20 from the shield blank 10 in accordance with the present invention includes the use of a shield blank holding fixture 22 especially constructed for placement on a conventional cutting table 24 of a band saw 26. The fixture 22 may be molded or fabricated in any suitable manner out of fiber glass, plastic, or the like and is comprised of a flat bottomed receptacle 28 having an upwardly facing concavity 30 presenting a rounded, shield blank supporting surface 32 provided with a radius of curvature complementary to the curvature of the bottom side 14 of the shield blank 10. An opening 34 is provided at the bottom center of the concavity 30 to provide clearance for a saw band 36. Reference to FIG. 4 of the drawing will clearly illustrate the complementary nature of the respective radii of curvature of the shield blank 10 and the blank-supporting surface 32 of the fixture 22.

Prior to the placement of the shield blank 10 in the concavity 30, a desired radiation field outline 38 corresponding to a predetermined area of a patient that is to be exposed to a field of radiation is drawn on a piece of paper or other sheet material 40. Initially the area to be exposed to a radiation field is outlined on an X-ray radiograph (not shown) of the patient by a radiotherapist and the outline as sketched is then reduced to the appropriate size on the paper 40 using a pantograph (not shown) resulting in the outline 38. It is, of course, to be understood that the degree of reduction of the outline is dependent upon the relative location of the completed focused shield 20 in a radiation therapy machine with respect to the source of the cobalt rays and relative location of the patient. The procedure employed in determing the extent of outline reduction and the relative distances involved between the patient and shield 20, as well as the distance from the shield 20 to the source of the radiation rays, is well known to those experienced in the field of rendering radiation treatments and will not be detailed herein.

Although it is not essential, it is desirable to cut the paper 40 to a size corresponding to that of the transverse dimensions of a radiation beam, which has a rectangular cross section at the point the latter strikes the top side 12 of the shield 20. In any event, the desired radiation field outline 38 is to be selectively placed on the paper 40 at a predetermined point relative to a center marking 42 representing the center of a radiation beam when the focused shield 20 is operably inserted in a radiation therapy machine.

Figure 1:
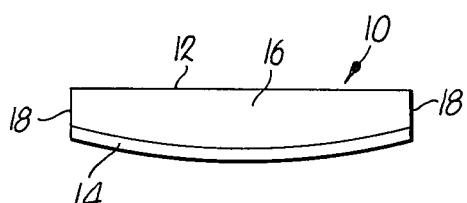
FIG. 1 is an elevational view of a focused shield blank having a rounded bottom wall made pursuant to the present invention.
Figure 2:
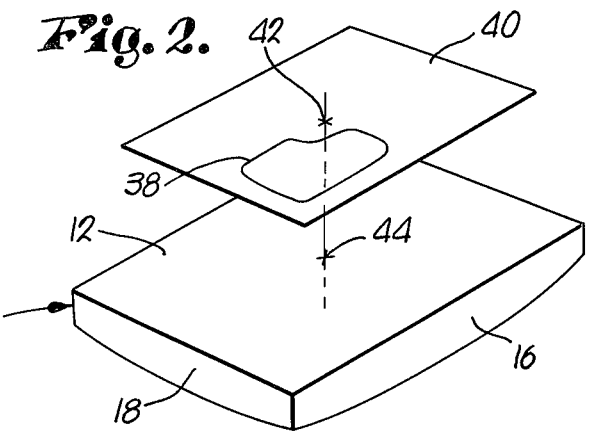
FIG. 2 is an exploded, top and edge perspective view of a focused shield blank and a piece of sheet material having a predetermined radiation field outline drawn thereon, the sheet material being spaced from the shield blank to illustrate the centering of the sheet material on the planar top side of the focused shield blank.
Figure 3:
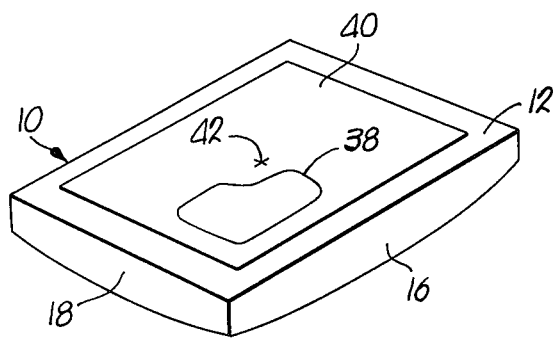
FIG. 3 is a perspective view similar to FIG. 2 showing the sheet material centrally positioned on the top side of the focused shield blank.

Once the radiation field outline 38 has been properly located on the paper 40 the latter is then placed on the top side 12 of the shield blank 10 such that the center marking 42 is superimposed over a predetermined center 44 of the shield blank 10 as shown in FIG. 2. Normally the paper 40 is pasted or otherwise secured to the top side 12 to insure that there is no inadvertent displacement of the outline 38 once the paper 40 has been positioned on the shield blank 10.

After the paper 38 has been secured to the top side 12, the shield blank 10 is positioned on the fixture 22 with the convexly rounded bottom side 14 of the shield blank 10 resting on the rounded, concave surface 32 of the bowl-shaped receptacle 28. Thus, it will be seen that as the shield blank 10 is normally manipulated, the actuated saw band 36 cuts an aperture 46 therein having a transverse configuration corresponding to that of the predetermined area of a patient to be exposed to a field of radiation as represented by the outline 38. Further, not only will the aperture 46 have the correct configuration, but the aperture 46 will also have beveled sidewalls 48 which are angularly disposed to be in parallelism with the angularity of the radiation rays passing through the aperture 46 adjacent the sidewalls 48 when the shield 20 is properly associated with a radiation therapy machine.

By way of further description it will be seen in referring to FIG. 4 that were the blank 10 positioned at the exact center of the concavity 30 any aperture sidewall located at this point would be perpendicular or normal to the top side 12 and be in alignment with the center of a radiation beam during use of the shield 20. Additionally, it will be further observed that when the blank 10 is shifted in any direction away from center, the angularity of the corresponding cut is increased in accordance with the increased angularity of the radiation rays as the outer perimeter of a radiation beam is approached with the sidewalls 48 diverging as the rounded bottom side 14 is approached.

Once the focused shield 20 has had the aperture 46 cut therein the focused shield is then securely attached to a mounting plate 50 by means of screws 52 for insertion into a radiation machine. The relative disposition of the focused shield 20, after it is inserted in a radiation machine, is depicted in FIG. 6 wherein the numeral 54 generally identifies a radiation beam as it would appear while emanating from a radiation source 56 of a radiation therapy machine.

It will be seen in referring to FIG. 6 that the shield 20 stops the radiation rays of any portion of the radiation beam 24 that is not in direct linear alignment with the aperture 46 while those rays, identified by the numeral 58 in alignment with the aperture 20 pass therethrough in an unimpeded manner. The unique construction of the focused shield 20, typified by the beveled aperture sidewalls 48, permits those rays 58 proximal thereto to pass through the aperture 46 in substantial parallelism with their respective adjacent sidewall 48. As is further apparent in viewing FIG. 6, the radiation rays will be precisely focused on the desired area of the patient for full exposure within the boundary of the outline 38. There will be no unintended "dead" spots beneath the shield 20 because the relative angularity of all portions of the sidewalls 48 is the same as that of the radiation rays passing thereby. The aperture 46 is, in effect, disposed within the shield 20 in axial alignment with the radiation rays 58 passing therethrough and no sections of the upper edge 60 of the aperture 46 block off any of the radiation rays 58. Likewise, none of the radiation rays 58 entering the aperture 46 strike any portion of the sidewalls 48 because of the parallelism of the same with the radiation rays 58. Manifestly, it is to be understood that all radiation rays 58 entering the aperture 46 at the top side 10 will exit in an unimpeded manner at the bottom side 14.

The angularity of the sidewalls 48 relative to the top side 12 is determined by the radius of curvature of the surface 32 and the rounded bottom wall 14. However, the required angularity of the sidewalls 48 and therefore the radius of the blank bottom side 14 and surface 32, needs to be calculated, keeping in mind the angle of divergence of the rays within the radiation beam 54.

While it is not necessary, the edges 16 and 18 of the blank 10 may also be trimmed to present beveled edges 16a and 18a as shown in FIGS. 5 and 6 to reduce the size of the finished focused shield 20 for purposes of weight reduction. However, in no event should the blank 10 be reduced to a size less than that of the paper 40 or the transverse width of the radiation beam 54 at the point it strikes the top side 12. It is to be further understood that the blank 10 is to be kept in full contact with the surface 32 during the cutting of the aperture 46 to insure the proper angularity of the sidewalls 48.

Once the blank 20 has been secured to the mounting plate 50 the focused shield 20 may be repeatedly used to treat a patient simply by inserting the assembled plate and shield into a radiation thereapy machine with the assurance that the exact same spot is being treated each time, that all rays in alignment with the aperture 46 enter the same, and that the rays exit the aperture in the exact same pattern they enter the aperture.

Having thus described the invention, what is claimed as new and desired to be secured by Letters Patent is:

1. A method of making a focused shield for use in connection with a radiation therapy machine or the like, said method comprising the steps of:
    forming a shield blank having a planar top side and an opposite, rounded bottom side;
    forming a shield blank holding fixture having a rounded shield blank supporting surface provided with a radius of curvature complementary to the curvature of the bottom side of said shield blank;
    selectively placing on the top side of said shield blank an outline having a configuration corresponding to a predetermined area of a patient to be exposed to a field of radiation;
    placing said fixture on a cutting table of a band saw or the like;
    positioning said shield blank on said fixture with the rounded bottom side of said shield blank resting on said rounded surface of said fixture; and
    cutting said shield blank along said outline with said saw or the like while maintaining the shield blank in contact with said rounded surface to provide a focused shield having a bevel-walled aperture corresponding to said predetermined area.

2. A method as claimed in claim 1, wherein said shield blank forming step includes shaping said bottom side to present a convexly rounded contour; and wherein the step of forming said shield blank holding fixture includes shaping said rounded surface to present a bowl-shaped concavity.

3. A method as claimed in claim 2, wherein said shield blank forming step includes premolding said shield blank in a rectangular shape having said planar top side and said convex bottom side.

4. A method as claimed in claim 1, wherein said step of placing said outline on said blank includes the step of drawing the desired radiation field boundary on paper or the like for placement on said shield blank.

5. A method as claimed in claim 4, wherein said step of placing said outline on said shield blank includes the step of indicating on said paper or the like the required location of the center of a radiation beam relative to said radiation field when the focused shield is properly inserted in a radiation therapy machine.

6. A method as claimed in claim 5, wherein said placement step further includes the step of positioning said paper or the like on said shield blank such that the indicated radiation beam center is superimposed over the center of the shield blank and is transversely centered relative to a radiation beam when said focused shield is inserted in a radiation therapy machine.

7. A method as claimed in claim 6; and the step of trimming the outer edges of said focused shield while the same is in said holding fixture to present a focused shield having beveled outer edges in angular alignment with the periphery of said radiation beam, said trimming step including reducing said focused shield to a size in which the perimeter of said top side encloses an area at least equal to that encompassed by the periphery of a radiation beam at the point the latter strikes said focused shield.

8. Apparatus for making a focused shield for use in connection with a radiation therapy machine or the like, said apparatus including:
    a focused shield blank having a planar top side and a rounded bottom side opposite said top side;
    a shield blank holding fixture having a rounded shield blank supporting surface provided with a radius of curvature complementary to the curvature of the bottom side of said shield blank; and
    means for placing at a predetermined location on the top side of said shield blank an outline representing a required boundary of a field of radiation and having a configuration corresponding to a predetermined area of a patient to be exposed to a field of radiation whereby a focused shield having a bevel-walled aperture with a transverse configuration corresponding to that of said predetermined area is provided when said shield blank is cut along said outline by a band saw or the like while maintaining the bottom side of said shield blank in contact with the rounded surface of said fixture.

9. Apparatus as claimed in claim 8, wherein said rounded bottom side has a convex contour, and wherein said rounded surface of said fixture presents a bowl-shaped concavity.

10. Apparatus as claimed in claim 8, wherein said outline placement means includes a piece of sheet material on which said outline is drawn, said outline displacement means further including means for retaining said sheet material on said top wall during the cutting of said aperture in said shield blank.

11. Apparatus as claimed in claim 10, wherein said sheet material has indicated thereon a marking representing the location of the center of a radiation beam when said focused shield is operably inserted in a radiation therapy machine, said outline being positioned on said sheet material at a predetermined location relative to said marking.

12. Apparatus as claimed in claim 11, wherein said sheet material is positioned on said top wall with said center marking on said sheet material superimposed over the center of said shield blank.

13. Apparatus as claimed in claim 12, wherein said sheet material is of a rectangular size having an area at least equal to that encompassed by the periphery of said radiation beam at the point the latter strikes said focused shield when the same is inserted in said therapy machine.

14. A focused shield for use in connection with a radiation therapy machine or the like, said focused shield comprising:
    a generally rectangular body having a planar top side and a rounded bottom side opposite said top side; and
    an aperture extending through said body from said top side to said bottom side and having a transverse irregular configuration corresponding to that of a predetermined area of a patient to be exposed to a field of radiation,
    said aperture being selectively located in said body and having beveled sidewalls for permitting those radiation rays in alignment with said aperture to enter the same and to pass therethrough unimpeded when said focused shield is operably inserted in a radiation therapy machine.

15. A focused shield as claimed in claim 14, wherein each aperture sidewall is in substantial parallelism with the path of travel of those radiation rays adjacent thereto.

16. A focused shield as claimed in claim 15, wherein said aperture sidewalls diverge as said bottom side is approached.

17. A focused shield as claimed in claim 14, wherein said body is of sufficient length and breadth to at least span the transverse width of a radiation beam at the point the latter strikes said focused shield when the same is operably inserted in said therapy machine.

* * * * *